United States Patent [19]
Brassart et al.

[11] Patent Number: 5,603,930
[45] Date of Patent: Feb. 18, 1997

[54] LACTOBACILLUS JOHNSONII CNCM I-1225

[75] Inventors: Dominique Brassart, Bussigny; Anne Donnet, Saint-Legier; Harriet Link, Vevey; Olivier Mignot, Blonay; Jean-Richard Neeser, Savigny; Florence Rochat, Montreux; Eduardo Schiffrin, Crissier, all of Switzerland; Alain Servin, Chatenay-Malabry, France

[73] Assignee: Nestec S.A., Vevey, Switzerland

[21] Appl. No.: 455,562

[22] Filed: May 31, 1995

Related U.S. Application Data

[63] Continuation of Ser. No. 430,264, Apr. 28, 1995, Pat. No. 5,494,664, which is a continuation of Ser. No. 84,525, Jun. 29, 1993, abandoned.

[30] Foreign Application Priority Data

Jul. 6, 1992 [EP] European Pat. Off. ............. 92810516

[51] Int. Cl.$^6$ .............................. C12N 1/20; A01N 63/08
[52] U.S. Cl. .................... 424/93.45; 435/252.9; 435/854; 426/61; 426/583; 426/584; 426/588; 426/580
[58] Field of Search ................................ 435/252.9, 854; 424/93.45; 426/61, 583, 587, 588, 580

[56] References Cited

U.S. PATENT DOCUMENTS

| | | |
|---|---|---|
| 3,953,609 | 4/1976 | Farr . |
| 4,147,773 | 2/1979 | Ogasa . |
| 4,314,995 | 2/1982 | Hata et al. . |
| 4,332,790 | 9/1982 | Sozzi et al. . |
| 4,396,631 | 3/1983 | Adachi et al. . |
| 4,689,226 | 8/1987 | Numri et al. . |
| 4,921,857 | 5/1990 | Heck et al. . |
| 4,946,791 | 8/1990 | Manfredi et al. . |
| 4,980,164 | 12/1990 | Manfredi et al. . |
| 4,985,246 | 1/1991 | Okonogi et al. . |
| 5,032,399 | 7/1991 | Gorbach et al. . |
| 5,116,821 | 5/1992 | Randall et al. . |
| 5,229,380 | 7/1993 | Harris . |
| 5,296,221 | 3/1994 | Mitsuoka ............... 424/93 J |

FOREIGN PATENT DOCUMENTS

| | | |
|---|---|---|
| 0199535 | 10/1986 | European Pat. Off. . |
| 05849 | 6/1989 | European Pat. Off. . |
| 09608 | 7/1991 | European Pat. Off. . |

OTHER PUBLICATIONS

Prescott & Dunn's, "Industrial Microbiology", 4th ed. 1982, Avi Publ. Co.

Patent Abstracts of Japan (vol. 13, No. 579): JP-A-12 42 532, Yakult Honsha Co. Ltd., Sep. 27, 1989.

Berg & Savage, Immune Responses of Specific Pathogen and Gnotobiotic Mice in Antigens of Indigenous and Non-indigenous Microorganisms. Infection and Immunity, vol. 11, Feb. 1975, pp. 320–329.

Biological Abstract No. 252134 (vol. 79): Ducluzeau, et al., Transfer of the Fecal Microbial Flora from Holoxenic Piglets and Adult Pigs to Axenic Piglets and Axenic Adult Mice; Effect of the Animal Host and of the Diet on the Fecal Microbial Pattern of these Animals. Ann Microbial (Paris) 1978, pp. 597–612.

Shahani, et al., Role of dietary lactobacilli in gastrointestinal microecology. The American Journal of Clinical Nutrition, vol. 33, Nov. 1980, pp. 2448–2457.

Perdigon, et al., Actividad Inmunopotenciadora de Bacterias Lacticas Administradas por via oral. Medicina (Buenos Aires). 46 (1986): 751–754.

Hotta, et al., Clinical Effects of Bifidobacterium Preparations on Pediatric Intractable Diarrhea. Keio J. Med., pp. 298–314, 1987.

Silva et al., Antimicrobial Substance from a Human Lactobacillus Strain. Antimicrobial Agents and Chemotherapy. Aug., 1987, 31(8), pp. 1231–1233.

Perdigon, et al., Systemic Augmentation of the Immune Response in Mice by Feeding Fermented Milks with *Lactobacillus casei* and *Lactobacillus acidophilus*, Immunology 63 (1988): pp. 17–23.

Driessen, et al., Fermented Milks with Selected Intestinal Bacteria: a healthy trend in new products, Neth. Milk Dairy J. 43 (1989) 367–382.

Bhatia, et al., *Lactobacillus acidophilus* Inhibits Growth of *Campylobacter pylori* In Vitro, Journal of Clinical Microbiology, vol. 27, No. 10, pp. 2328–2330 (1989).

Perdigon, et al., Prevention of gastrointestinal infection using immunobiological methods with milk fermented with *Lactobacillus casei* and *Lactobacillus acidophilus*. Journal of Dairy Research, 57, (1990), 255–264.

Goldin, et al., Survival of Lactobacillus Species (Strain GG) in Human Gastrointestinal Tract, Digestive Diseases and Sciences. vol. 37, No. 1 (Jan. 1992) pp. 121–128.

Medline Database Abstract No. 92253433: Balli, et al., Batterioterapia orale ad alte dosi nella diarrea cronica aspacificia del bambino. Pediatr Med Chir (Italy). Jan.–Feb. 1992, 14(1), pp. 13–15.

Chauviére, et al., Adhesion of human *Lactobacillus acidophilus* Strain LB to Enterocyte–Like Caco–2 Cells. Journal of General Microbiology, 138 1689–1696 (1992).

Bazzoli, et al., In Vivo *Helicobacter pylori* Clearance Failure with *Lactobacillus acidophilus*. Gastroenterology, vol. 102, No. 4, Part 2, AGA Abstracts pp. A38 (1992).

Coconnier, et al., Protein–Mediated Adhesion of *Lactobacillus acidophilus* BG2F04 on Human Enterocyte and Mucus–Secreting Cell Lines in Culture. Applied and Environmental Microbiology, vol. 58, No. 6, pp. 2034–2039 (1992).

(List continued on next page.)

*Primary Examiner*—Irene Marx
*Attorney, Agent, or Firm*—Vogt & O'Donnell, LLP

[57] ABSTRACT

*Lactobacillus johnsonii* strain CNCM I-1225 adheres to Caco-2 cells and inhibits adhesion thereto by enterovirulent and enteroinvasive pathogens.

10 Claims, No Drawings

OTHER PUBLICATIONS

Chauviére, et al., Competitive exclusion of diarrheagenic *Escherichia coli* (EtEC) from human enterocyte–like Caco–2 cells by heat killed Lactobacillus. FEMS Microbiology Letters 91:213–218 (1992).

Midolo, et al., Lactobacilli and Related Organisms have Activity Against *Helicobacter pylori* In Vitro. Gastroenterology, vol. 104, No. 4, Part 2. AGA Abstracts p. A746 (1993).

Lidbeck, et al., Lactobacilli, anticarcinogenic activities and human intestinal microflora. European Journal of Cancer Prevention. vol. 1:341–53 (1992).

Gonzalez, et al., Inhibition of Enteropathogens by Lactobacilli Strains Used in Fermented Milk. Journal of Food Protection, vol. 56, No. 9 pp. 773–776 (Sep. 1993).

Coconnier, et al., Inhibition of adhesion of enteroinvasive pathogens to human intestinal Caco–cells by *Lactobacillus acidophilus* strain LB decreases bacterial invasion. FEMS Microbiology Letters 110:299–306 (1993).

Nader de Macias, Prevented of Infections Produced by *Escherichia coli* and *Listeria monocytogenes* by Feeding Milk Fermented with Lactobacilli. Journal of Food Protection vol. 56, No. 5 pp. 401–405 (1993).

LACTOBACILLUS JOHNSONII CNCM I-1225

CROSS REFERENCE TO RELATED APPLICATION

This application is a continuation application of Ser. No. 08/430,264, filed Apr. 28, 1995, now U.S. Pat. No. 5,494,664, which is a continuation application of Ser. No. 08/084,525, filed Jun. 29, 1993, now abandoned.

This invention relates to a biologically pure culture of a lactic acid bacterium strain, to a composition containing this strain and to the use of the strain.

European Patent Application Publication No. 199 535 (Gorbach and Goldin) proposes a bacterial strain identified in the first instance as being a *Lactobacillus (L.) acidophilus*, but then as bearing more of a resemblance to *L. casei* subs. *ramnosus* (cf. M. Silva et al. in Antimicrobial Agents and Chemotherapy, 31, No. 8, 1231–1233, 1987), which shows good adhesion to the cells of the mucus of the small intestine and which lends itself to therapeutic applications. This strain, baptized "strain GG" and lodged in the ATCC (American Type Culture Collection) under No. 53103, may be used in conjunction with a pharmaceutically acceptable support, more particularly in food products, above all in acidified milk products of the yogurt type for example.

Other strains of the same type have long been used in analogous products and with analogous objectives. However, there is a need for particularly high-performance strains of this type which could be clearly identified, which would have indisputable advantages and which would enrich the range of available strains.

The problem addressed by the present invention was to satisfy this need.

SUMMARY OF THE INVENTION

The present invention provides a biologically pure culture of a strain of lactic acid bacterium selected for its affinity for implantation in an intestinal flora, for its ability to adhere to intestinal cells, for its capacity for competitive exclusion of pathogenic bacteria from intestinal cells and for its capacity for immunomodulation and/or reduction of fecal enzymatic activity.

The strain in question is particularly intended for administration to human beings or animals for therapeutic or prophylactic treatment of the gastrointestinal system, more particularly as an antidiarrhoeic.

The strain may be administered in the form of a biologically pure culture, for example as such, after freezing and/or freeze-drying. The culture in question may comprise, for example, $10^8$ to $10^{10}$ viable germs (cfu from the technical English expression "colony forming units") per g for the liquid or frozen form and $10^9$ to $10^{11}$ cfu/g for the freeze-dried form.

The strain may also be administered in the form of a composition containing the culture and an ingestible support, more particularly a pharmaceutically acceptable support or a food product such as, for example, an acidified milk, more particularly a yogurt or a milk-based powder formulation.

DETAILED DESCRIPTION OF THE INVENTION

In a first preferred embodiment, the invention provides a culture of a strain of lactic acid bacterium selected for its affinity for implantation in the digestive tube of mice or rats with human intestinal flora.

In a second preferred embodiment, the invention provides a culture of a strain of lactic acid bacterium selected for its capacity for competitive exclusion of the pathogenic bacteria responsible for diarrhoea from intestinal cells.

Among various strains of bacteria thus selected in particular from acidified milks, particularly commercial yogurts, or from commercial cultures intended for the preparation of such milks or from the feces of infants for example, four were lodged by way of example under the Budapest Treaty on the Jun. 30, 1992 in the Collection Nationale de Cultures de Microorganismes (CNCM), Institut Pasteur, 28 rue de Dr. Roux, 75724 Paris Cedex 15, France, where they were each given the respective CNCM number shown in brackets below, namely a strain of *Lactobacillus acidophilus* (CNCM I-1225), a strain of *Bifidobacterium breve* (CNCM I-1226), a strain of *Bifidobacterium infantis* (CNCM I-1227) and a strain of *Bifidobacterium longum* (CNCM I-1228).

Subsequent to deposit of strain CNCM I-1225, the taxonomic classification of *Lactobacillus acidophilus* was reorganized to include six subgroups or "genomospecies." See Fujisawa, et al., Taxonomic Study of the *Lactobacillus acidophilus* Group with Recognition of *Lactobacillus gallinarum* sp nov and *Lactobacillus johnsonii* sp nov and Synonymy of *Lactobacillus acidophilus* Group A3 with the Type Strain of *Lactobacillus amylovorous*, Int. J. Syst. bacteriol. 42:487:491 (1992). Subsequent to that taxonomic reclassification, it was determined by species-specific DNA probe ("Lbj") that strain CNCM I-1225 is a member of the newly established *Lactobacillus johnsonii* species.

Details of the morphology and general properties of these strains are given in the following:

*L. johnsonii* CNCM I-1225

Morphology:
Gram-positive microorganism, non-motile, non-sporing.
Isolated, fairly short and thick rodlets.

Metabolism
Microaerophilic microorganism with homofermentative metabolism giving rise to the production of L(+) and D(−) lactic acid.

Other characteristics: catalase (−), production of $CO_2$ (−), hydrolysis of arginine (−).

Fermentation of sugars:
Amygdaline (+), arabinose (−), cellobiose (+), esculine (+), fructose (+), galactose (+), glucose (+), lactose (+), maltose (+/−), mannitol (−), mannose (+), melibiose (−), raffinose (+), ribose (−), salicine (+), sucrose (+), trehalose (+).

*B.Breve* CNCM I-1226. *B. infantis* CNCM I-1227 and *B. longum* I-1228

Morphology:
Gram-positive microorganisms, non-motile, non-sporing.
Short rodlets with rounded ends and "V" or "Y" branches.

Metabolism:
Anaerobic microorganisms with heterofermentative metabolism giving rise mainly to the formation of lactic and acetic acid.

Other characteristics: catalase (−), production of $CO_2$ (−), hydrolysis of arginine (−).

Fermentation of sugars
Since the sugar fermentation profile of these species is very unstable and non-reproducible, only a few sugars are always fermented, particularly D-ribose, lactose and raffinose.

Details of the particular properties for which the present strain may be selected are given below:

Implantation in an intestinal flora
Gnotoxenic mice

Two groups of axenic mice (mice without intestinal flora) are each associated with the human flora of a different donor (gnotoxenic mice). After several days' acclimatization, the intestinal flora of the mice are entirely comparable with those of the human donors from the functional, qualitative and quantitative viewpoints.

According to the invention, numerous strains have been tested for their ability to colonize the digestive tube of these mice with human flora, i.e. for their affinity for implantation in this intestinal flora.

It was found that most of the strains are not capable of colonizing these animals even after several successive inoculations, although the L. johnsonii strain CNCM I-1225, for example, was capable of proliferation and implantation in the digestive tube, i.e. in the intestinal flora of the mice of the two groups, even after a single inoculation.

This colonization or implantation enables the strain to be present in the feces in quantities of more than $10^6$ cfu/g. This content of viable germs of the strain in the feces may be considered as necessary and/or sufficient for the metabolism of the strain to be able to modify that of the host.

It was also found that this implantation persists as long as the environment of the animals is not disturbed.

Gnotoxenic rats

Axenic rats are associated (gnotoxenic rats) with an isolated strain (*Bacteroides thetaiotamicron* FI 1, particular collection of the Centre de Recherche Nestec SA, CH-1000, Lausanne, Switzerland) of a human intestinal flora of a healthy donor intended, as will be seen hereinafter, to simulate the production of enzymes of a complete fecal flora. This association results in abundant colonization of the intestine of these rats so that the bacterium is present in the feces in quantities of approximately $10^8$ cfu/g.

An implantation test of the L. johnsonii strain CNCM I-1225, for example, in this flora results in good co-colonization so that the strain is also present in the feces in quantities of approximately $10^8$ cfu/g.

Human volunteers

The number of viable germs of L. bulgaricus appearing in the feces of healthy human volunteers who ate traditional yogurt prepared by fermentation of a cow's milk with a commercial culture of L. bulgaricus and S. thermophilus was determined by way of comparison.

The volunteers did not eat any fermented milk product for three consecutive periods of three weeks each except for the yogurt which they ate during the second three-week period.

In the three weeks when they ate yogurt, they did so in such a way as to ingest approximately $10^{10}$ L. bulgaricus per day which corresponded to approximately three 120 g yogurts per day. During the period of consumption of the yogurts, the feces of the volunteers were found to contain approximately $10^5$ cfu of L. bulgaricus per g.

According to the invention, a test was conducted in the same scenario as above, but with yogurt prepared by fermentation of a milk with a commercial culture of S. thermophilus and B. bifidus supplemented, for example, with the L. johnsonii strain CNCM I-1225 in a concentration of the same order.

The total number of viable germs of lactobacilli in the feces of the volunteers was determined before, during and after the period of consumption of the yogurt. Values of $10^5$ to $10^6$ cfu/g were found before, values of more than $10^7$ cfu/g during and values of $10^6$ cfu/g after the period of consumption.

Accordingly, there was an increase in the total number of lactobacilli found in the feces during the period of consumption of the yogurt. The CNCM I-1225 strain was found in a significant quantity and in viable form in the volunteers. By contrast, it was eliminated in a few days after the volunteers stopped eating the yogurt.

Reduction of fecal enzymatic activity
Gnotoxenic rats

The fecal azoreductase and nitroreductase activity was determined in tests conducted with the gnotobiotic rats mentioned above. This was because the enzymes azoreductase and nitroreductase were involved in the production of carginogenic substances. A high concentration of these enzymes is associated with an increased risk of cancer of the colon.

It was found that the fecal enzymatic activity of the gnotobiotic rats with Bacteroides rose to 2.5 µg/h/mg protein for azoreductase and to 4.2 µg/h/mg protein for nitroreductase whereas, for the gnotobiotic rats with Bacteroides in the flora of which the CNCM I-1225 strain, for example, had been implanted, this enzymatic activity rose to 1.8 µg/h/mg protein for azoreductase and to 3.5 µg/h/mg protein for nitroreductase.

In addition, it was found that gnotobiotic rats with intestinal flora formed exclusively from the CNCM I-1225 strain showed no fecal azoreductase or nitroreductase activity.

In other words, the presence of the CNCM I-1225 strain in the flora of gnotobiotic rats induces a reduction in the production of certain undesirable enzymes in these animals, i.e, beneficial modifications in the metabolism of the host.

Human volunteers

Fecal nitroreductase activity was determined in the above-mentioned tests carried out with human volunteers. This activity was determined during the last days preceding the period of consumption of yogurt prepared, for example, with the CNCM I-1225 strain, throughout that period and for the first few days following it.

It was found that this activity changed from 8.2 to 4.9 µg/h/mg protein during the period of consumption of the yogurt, remained at that level for about one week after that period and then increased progressively increased.

Immunomodulation
Human volunteers (phagoytic power of leucocytes)

Human volunteers abstained from eating fermented milk products except for the products eaten in accordance with the following program: milk for three weeks, yogurt prepared by fermentation of a milk with a mixed culture of commercial S. thermophilus and L. acidophilus CNCM I-1225, for example, for the following three weeks and then milk for six weeks.

The phagycytic power of the leucocytes in the peripheral blood of the volunteers was determined at the beginning and at the end of each of these periods.

This determination comprises extracting the leucocytes from the blood and bringing them into contact with fluorescent bacteria. The fluorescent light emitted by the leucocytes which had phagocytosed the fluorescent bacteria was measured by cytometric analysis in flux (using an apparatus of the type commercially available under the name of Facscan). The percentage of leucocytes showing phagocytic activity, i.e. the phagocytic power mentioned above, was deduced therefrom.

A phagocytic power of the leucocytes in the peripheral blood of 36.5% was observed at the beginning of the first period of consumption of milk 32.7% at the end of that period and hence at the beginning of the period of consumption of yogurt, 51.8% at the end of the period of consumption of yogurt and 51.4% six weeks afterwards, i.e. at the end of the second and last period of consumption of milk. The probability of an error being made (p value) by estimating that this increase in the phagocytic power of the leucocytes is significant is less than 0.1%.

Human volunteers (response to a vaccine)

16 Healthy human volunteers (test group) followed the following eating program: for two weeks (weeks 1 and 2), normal diet excluding any fermented product; for the following three weeks (weeks 3, 4 and 5), mixed diet of three 125 ml yohurts per day, the yogurts having been prepared by fermentation of a milk with a commercial culture of *S. thermophilus* and *Bifidobacterium bifidus* to which the *L. johnsonii* strain CNCM I-1225—present in this yogurt—was added in a quantity of $10^7$ to $10^8$ cfu/ml; and for another two weeks (weeks 6 and 7) normal diet excluding any fermented products.

14 Healthy human volunteers (control group) simultaneously followed an eating program consisting of a normal diet excluding any fermented product.

A vivotive oral vaccine (*Salmonella typhi* Ty21a) marketed by Berna SA was administered to the volunteers of the two groups in accordance with the manufacturer's instructions on days 1, 3 and 5 of week 4.

Blood samples were taken from all the volunteers 3 days after the beginning of week 3 and 1 day and 10 days after the end of week 5.

Determination of the concentration of the specific IgA's of the immune response to the antigenic lipopolysaccharides (LPS) of *Salmonella typhi* was carried out by the ELISA method.

It was found that the increase in the concentration of the specific IgA's observed fifteen days after vaccination in relation to the concentration observed nine days before vaccination is significant in the two groups (p value >0.001).

However, if ranges of increase factors <2; >2 and <3; >3 and <4; >4 are taken into consideration, respective distributions are observed in these ranges of 1, 6, 3 and 6 volunteers for the test group against 8, 3, 0 and 3 volunteers for the control group. In other words, the increase factors are significantly higher in the test group than in the control group (p value=0.04).

Adhesion to intestinal cells

According to the invention, a study was made of the adhesion of various strains of lactic acid bacteria to intestinal cells, more particularly to Caco-2 human epithelial intestinal cells (M. Pinto et al., Biol. Cell. 47, 323, 1983) and to mucus-secreting human intestinal cells HT29-MTX (Lesuffleur et al., Cancer Res. 50, 6334–6343) in a monolayer culture in vitro.

To this end, the cells were cultured in 25 cm² plastic bottles (Corning) for maintaining the cell lines and on degreased and sterilized glass slips (22×22 mm) placed in 6-cup trays (Corning) for the adhesion tests.

To cultivate the Caco-2 and HT29-MTX cells, the medium had to be changed daily from the second day after reseeding. The culture medium was prepared from Eagle minimum essential medium powder modified with Dulbecco (DMEM).

The lactic bacteria were cultured in anaerobiosis on MRS medium from a frozen stock. The bacteria were used from the second subculture.

A mixed medium for incubation on the cells was prepared by mixing 50% of a DMEM medium without antibiotic and 50% of the MRS medium in which the bacteria had grown, this medium containing $10^8$ lactobacilli or bifido bacteria (cf. Chauvière G. et al., FEMS Microbiol. Lett. 91, 213–218, 1992).

To carry out the adhesion test, the mixed medium containing the bacteria was placed on the intestinal cells and incubated for one hour in aerobiosis. The multiple-cup trays were washed five times by twenty circular agitations to enable the non-adhering bacteria to be effectively eliminated. The cell lawns were then fixed in successive baths of methanol, 10 mins. at 70%, 10 mins. at 95% and 15 mins. at 100%, and coloured with Gram or Giemsa coloration. An adhesion level was determined by counting the adhering bacteria under a microscope.

Among the numerous strains tested, the four strains lodged by way of example for the purposes of the present invention showed a good level of adhesion to intestinal cells as determined by these adhesion tests on the Caco-2 cell line.

Thus, the *L johnsonii* strain CNCM I-1225 adhered to the Caco-2 cells to a level of approximately 150+23 bacterium cells per 100 Caco-3 cells. If this result is given a score of +++++, an adhesion of ++++++ is obtained for *B. breve* CNCM I-1226, a score of ++++ for *B. infantis* CNCM I-1227 and a score of ++++ for *B. longum* CNCM I-1228.

Tests to determine the adhesion of the *L-johnsonii* strain CNCM I-1225, for example, to the HT29-MTX cells produced even more spectacular results.

It was also surprisingly found that the adhesion of these strains or at least some of them was due to a factor which they secrete in their own culture medium (MRS or milk for example). Thus, when the process of incubation for 1 hour on Caco-2 described above was carried out with the strains *L. johnsonii* CNCM I-1225, *B. breve* CNCM I-1226 or *B. longum* CCNCM I-1228 without their bacterial culture medium, a significant reduction in adhesion was observed.

In addition, when this process of incubation was carried out on Caco-2 with these strains and their culture medium subjected beforehand to treatment with trypsin, a significant reduction in adhesion was again observed. This would appear to prove that the adhesion factor secreted by these strains in their culture medium is a protein.

Competitive exclusion of pathogenic bacteria

According to the present invention, a study was made of the various lactic acid bacterium strains for their capacity for competitive exclusion of pathogenic bacteria, more particularly the pathogenic bacteria responsible for diarrhoea, from intestinal cells.

In particular, a study was made of the exclusion of certain saprophytic strains of *E. coli* from the digestive tube of human beings and animals which can assume a virulent character and can become pathogenic, namely enterotoxinogenic *E. coli* (ETEC), enteroadherent *E. coli* (DAEC) and enteropathogenic *E. coli* (EPEC), and of the exclusion of a strain of *Salmonella typhi-murium*.

The strains used for this study are as follows:

for ETEC, the strain H10407 which expresses CFA/1 (Collection of Professeur Joly, Laboratoire de Microbiologie, Faculté de Médecine et de Pharmacie, Université de Clermont-Ferrand 1, 63003 Clermont-Ferrand, France)

for DAEC, the strain C1845 (collection of Dr. S. Bilge, Department of Microbiology, School of Medicine, G 3111 Health Sciences Building, University of Washington, Seattle, Wash. 98195, USA)

for EPEC, the strain JPN15 pMAR7 which expresses EAF and eae (collection of Prof. J. Kaper, Center for Vaccine Development, University of Maryland, School of Medicine, 10 South Pine Street, Baltimore, Maryland 21201, USA)

for *Salmonella typhi-murium*, the strain SL 1344 (Dr. B. Stocker, Stanford University, School of Medicine, Department of Microbiology and Immunology, Sherman Sairchild Science Building, D 333 Stanford, Calif. 94305–5402, USA).

The adhesion of the bacteria to the Caco-2 cells was determined as follows:

Briefly, the monolayers of Caco-2 cells were washed twice with a saline phosphate buffer (PBS). The $^{14}$C-labelled *E. coli* or the $^{35}$S-labelled *Salmonella* were suspended in the culture medium in a quantity of $10^8$ cfu/ml and 2 ml suspension were added to each cup containing a slip bearing the cell culture.

For *E. coli*, the incubations were all carried out in the presence of 1% D-mannose. To determine an exclusion factor or level, i.e. the proportion of pathogenic bacteria prevented from adhering to the Caco-2 cells by lactic bacteria which take their place, 1 ml suspension containing $10^8$ cfu/ml labelled pathogenic strain and 1 ml of a suspension containing either $10^8$ or $10^9$ cfu/ml of the lactic acid bacterium strain tested were added to each cup containing a slip bearing the cell culture.

The plates are incubated for 1 hour at 37° C. in an atmosphere of 10% $CO_2$ and 90% air. The monolayers of cells are washed 5 times with sterile PBS. The adhering bacteria and the intestinal cells are dissolved in 0.2 N NaOH solution. The number of labelled adhering bacteria is evaluated by liquid scintillation counting.

Among the various strains of lactic bacteria thus tested for their performance properties or for their capacity for competitive exclusion of pathogenic bacteria, the strains selected and lodged by way of example for the purposes of the present invention produced remarkable results as set out in the following Table which shows in % the exclusion levels achieved by the strains tested at the expense of the various pathogenic strains used in these tests.

| Strain (CNCM No.) | Concentration (cfu/ml) | Competitive exclusion factor (%) with respect to: | | | |
|---|---|---|---|---|---|
| | | ETEC | DAEC | EPEC | Salmonella |
| I-1225 | $10^9$ | 78 | 79 | 83 | 86 |
| | $10^8$ | 50 | 53 | 53 | 42 |
| I-1226 | $10^9$ | 80 | 68 | 83 | 88 |
| | $10^8$ | 55 | 53 | 55 | 41 |
| I-1228 | $10^9$ | 47 | 47 | | |
| | $10^8$ | 11 | | | |
| I01227 | $10^9$ | 58 | 46 | | |
| | $10^8$ | 18 | | | |

We claim:

1. A biologically pure culture of *Lactobacillus johnsonii* strain CNCM I-1225.

2. A cell-free culture supernatant isolated from a biologically pure culture of *Lactobacillus johnsonii* strain CNCM I-1225.

3. A food composition comprising an ingestible support and a culture of *Lactobacillus johnsonii* strain CNCM I-1225.

4. A food composition according to claim 3 wherein the ingestible support is an acidified milk product.

5. A food composition according to claim 3 wherein the ingestible support is a yogurt.

6. A food composition according to claim 3 wherein the ingestible support is a milk-based powder.

7. A food composition comprising an ingestible support and a cell-free culture supernatant isolated from a biologically pure culture of *Lactobacillus johnsonii* strain CNCM I-1225.

8. A food composition according to claim 7 wherein the ingestible support is an acidified milk product.

9. A food composition according to claim 7 wherein the ingestible support is a yogurt.

10. A food composition according to claim 7 wherein the ingestible support is a milk-based powder.

* * * * *

UNITED STATES PATENT AND TRADEMARK OFFICE
CERTIFICATE OF CORRECTION

PATENT NO. : 5,603,930
DATED : February 18, 1997
INVENTOR(S) : Dominique Brassart, et al.

It is certified that error appears in the above-indentified patent and that said Letters Patent is hereby corrected as shown below:

On the title page, under the heading "[56] References Cited, Foreign Patent Documents", delete "05849  6/1989  European Pat. Off. .
       09608  7/1991  European Pat. Off. ."

and insert therefor

—WO 05849    6/1989    WIPO.
      WO 09608    7/1991    WIPO.—.

Col. 4, line 48, change "acidophilus" to —johnsonii—.

Signed and Sealed this

Twenty-sixth Day of August, 1997

Attest:

BRUCE LEHMAN

*Attesting Officer*      *Commissioner of Patents and Trademarks*